United States Patent [19]

Hollander et al.

[11] Patent Number: 4,876,191

[45] Date of Patent: Oct. 24, 1989

[54] IMMOBILIZATION OF BIOLOGICALLY ACTIVE SUBSTANCES WITH CARRIER BOND ANTIBODY

[75] Inventors: Zeev Hollander, Herzlia; Beka Salomon, Herzlia Pituach; Ephraim Katchalski-Katzir, Rehovot, all of Israel

[73] Assignee: Ramot University Authority for Applied Research and Industrial Development Ltd., Tel-Aviv, Israel

[21] Appl. No.: 885,155

[22] Filed: Jul. 14, 1986

[30] Foreign Application Priority Data

Jul. 17, 1985 [IL] Israel ................................ 75828

[51] Int. Cl.$^4$ ................ G01N 33/573; G01N 33/543; C12P 1/00; C12N 11/00
[52] U.S. Cl. .......................................... 435/7; 435/24; 435/26; 435/41; 435/174; 435/176; 435/178; 435/180; 436/518; 436/524; 436/531; 436/548
[58] Field of Search ............... 436/513, 524, 530, 531, 436/518, 548; 435/7, 24, 26, 41, 814, 815, 174, 177, 176, 178

[56] References Cited

U.S. PATENT DOCUMENTS

| 4,002,532 | 1/1977 | Weltman et al. | 436/530 X |
| 4,048,298 | 9/1977 | Niswender | 436/530 X |
| 4,433,059 | 2/1984 | Chang et al. | 436/824 X |
| 4,693,985 | 9/1987 | Degen et al. | 436/824 X |

FOREIGN PATENT DOCUMENTS

8303678 10/1983 PCT Int'l Appl. ................. 436/824

OTHER PUBLICATIONS

Srivastara, et al., Journal of Biochemical and Biophysical Methods, vol. 2, 1980, pp. 1-9.
"Immunodiffusion and Immunoelectrophoresis", O. Ouchterlony et al., in Handbook of Experimental Immunology, D. M. Weir, Ed., vol. 1, pp. 19.1-19.5, Blackwell, Canada, 1978.
"The Kinetics of Some Carboxypeptidase A and Acetylcarboxypeptidase A Catalyzed Hydrolses," J. R. Whitaker et al., Biochemistry, vol. 5, No. 1, 1968, pp. 386-392.
"A Rapid and Sensitive Method for the Quantitation of Microgram Quantities of Microgram Quantities of Protein Utilizing the Principle of Protein-Dye Binding," M. M. Bradford, Analytical Biochemistry, 72, 248-254, 1976.
"Immunoassay Using Antigen-Enzyme Conjugates," B. K. Van Weeman et al., FEBS Letters, vol. 15, No. 3, pp. 232-236, Jun. 1971.
"Continous Cultures of Fused Cells Secreting Antibody of Predefined Specificity," G. Kohler et al., Nature, vol. 256, pp. 495-497, Aug. 7, 1975.
"A Rapid Method of Preparing Pure Serum Gamma-Globulin," D. R. Stanworth, Nature, vol. 188, pp. 156-157, Oct. 8, 1960.
"Interaction of Carboxypeptidase A with Monoclonal Antibodies," Beka Solomon et al., Molecular Immunlogy, vol. 21, No. 1, pp. 1-11, 1984.

(List continued on next page.)

Primary Examiner—David M. Naff
Attorney, Agent, or Firm—Fleit, Jacobson, Cohn, Price, Holman & Stern

[57] ABSTRACT

The invention relates to compositions which are capable of selectively binding a biologically active protein, retaining its activity. Such compositions have essentially three parts, linked together: a water-insoluble carrier, an antibody bound by the carrier and being against the Fc region of an immunoglobulin and an antibody bound thereto which is specific towards the protein which is to be bound to this composition. Proteins of choice are enzymes and isoenzymes such as carboxypeptidas A or isoenzyme 5 of porcine lactate dehydrogenase. Preferably the antibody bound to the carrier is a polyclonal anti-mouse antibody and the antibody bound thereto is a monoclonal mouse antibody. Based on such compositions, there is provided an assay for the quantitative determination of such proteins.

8 Claims, 1 Drawing Sheet

OTHER PUBLICATIONS

"High Frequencies of Antigen-Specific Hybridomas: Dependence on Immunization Parameters and Prediction by Spleen Cell Analysis," C. Stahli et al., Journal of Immunological Methods, 32 (1980) 297–304.

"Preparation of Adsorbents for Biospecific Affinity Chromatography . . . " L. Sundberg et al., Journal of Chromatography, 90 (1974) 87–98.

"Nephelometric Activity as a Criterion of Adequate Antisera for use in Immunofluorescence," J. Gauldie, et al., Int. Archs Allergy Appl. Immun. 60: 186–194 (1979).

"Isolation of Pure $IgG_1$, $IgG_{2a}$ and $IgG_{2b}$ Immunoglobulins from Mouse Serum Using Protein A-Sepharose," P. L. Ey et al., Immunochemistry, vol. 15, pp. 429–436, 1978.

"Lactate Dehydrogenase," in the Enzymes, 3rd Ed., P. O. Boyer, Ed., vol. XI, pp. 191–292, 1975.

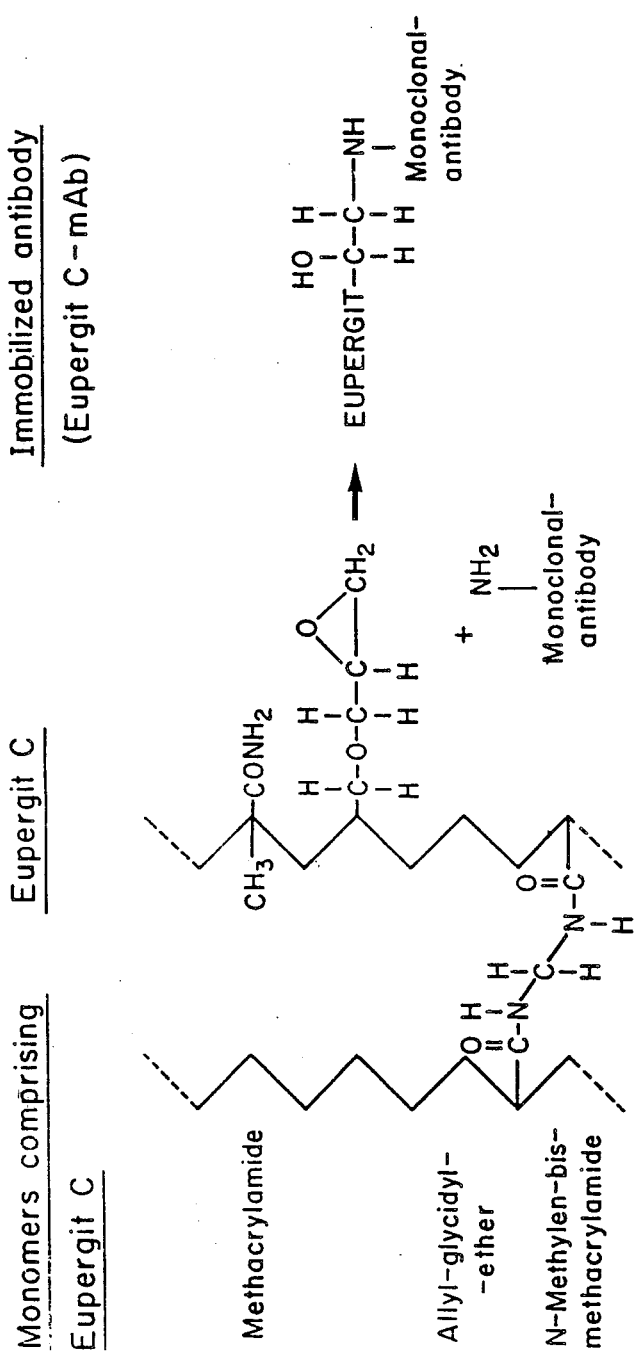
Fig. 1: Scheme describing the preparation of the Eupergit C—Monoclonal-antibody conjugate.

IMMOBILIZATION OF BIOLOGICALLY ACTIVE SUBSTANCES WITH CARRIER BOND ANTIBODY

FIELD OF THE INVENTION

There are provided compositions of matter adapted to bind specifically a predetermined biologically active protein while retaining such biological activity, said composition comprising a water-insoluble carrier to which there is chemically bound an antibody against the Fc region of an immunoglobulin, to which there is bound by an immunochemical bond an antibody which is specific towards the biologically active protein.

The proteins of choice are enzymes, the biological activity of which is maintained to a very large extent, and this mainly due to the following reasons:

a. The anti-enzyme antibodies are selected in such manner as to bind firmly to the enzyme without influence on the enzymatic activity;

b. The attachment of the enzyme molecules to the solid phase (which in many cases is "hostile" in a biological sense) is via a long spacer which is located between the carrier and the active part of the enzyme molecule.

The carrier-antibody against Fc region of immunoglobulin conjugate can be used for bonding to same a variety of specific antibodies, each of which is specific towards a desired biologically active protein. Such protein can thus be extracted from liquids, including body fluids, and determined.

Carrier bound proteins, such as enzymes, can be used in column form for effecting enzymatic processes.

BACKGROUND OF THE INVENTION

Carrier bound enzymes are well known since the pioneer work of Katchalsky and Bar-Eli. Such enzymes are widely used in various fields and also in large scale industrial processes. In medicine the quantitative measurement of certain enzymes in body fluids is an important diagnostic tool. The level and types of enzymes present are indicative of various states of pathological conditions, some of which cannot be detected and determined by other means. Various methods are in use for determining enzymes and isoenzymes, such as measurements of specific enzymatic activity, if necessary in the presence of inhibitors or activators so as to differentiate between isoenzymes; the use of separation techniques adapted to separate enzymes and isoenzymes, and the subsequent determination of these; immunodetermination of enzymes based on the specific antibodies. Most of the conventional techniques are rather cumbersome and expensive.

The use of monoclonal antibodies provides for a high degree of specificity of such assays, it is possible to prepare a great variety of monoclonal antibodies directed towards specific, welldefined antigenic sites of a given protein. The state of the art, suggests that it is possible to prepare monoclonal antibodies specific to various enzymes with a high affinity without adversely affecting the enzymatic activity. Antibodies bonded to a carrier are specific for a given enzyme. The present invention obviates a number of the drawbacks of existing systems of carrier bound biologically active proteins and provides valuable means for use in diagnosis and also for use in industrial processes where carrier bound proteins, and especially enzymes, are used.

SUMMARY OF THE INVENTION

There are provided compositions of matter adapted to bind bio-active molecules, such as biologically active proteins or other entities adapted to elicit antibody formation when injected into suitable laboratory animals. The compositions of the invention consist of a three-component conjugate A-B-C-, where A designates a water-insoluble carrier, B designates an antibody against the Fc-region of an immunoglobulin, to which there is bonded via an immuno-chemical bond an antibody, C which is specific to the entity which is to be attached to the A-B-C- conjugate. When this is a bioactive molecule such as an enzyme, such enzyme may be extracted from a liquid system, such as body fluids, in a quantitative manner and it can be determined in a quantitative manner. There can also be provided a column of carrier bound active proteins, such as enzymes, A-B-C-E, where E designates such active protein (enzyme), and such columns can be used for carrying out enzymatic processes. There can also be used carrier bound entities A-B-C-E, where A is in bead form, or other particulate form, and where the enzymatic process is carried out by contacting the substrate with such carrier bound enzyme in particulate form.

In the following the invention will be described with reference to biologically active proteins, and especially enzymes. It ought to be understood that it applies also to any other suitable type of bio-active molecule.

The novel compositions can be used for analytical purposes, such as determinations of the active entity (protein, and more specifically enzyme); they can also be used for purposes where a carrier bound entity is advantageous: thus, for example, there can be provided columns of carrier-bound active proteins (enzymes and the like) which make it possible to carry out certain conversions, and in case of enzymes, enzymatic processes.

In the following the invention is illustrated with reference to enzymes, but it ought to be clearly understood that this is by way of illustration only and that other haptens (active proteins and other entities, adapted to elicit antibody formation), can be used as well.

The bond A-B is generally a stable one, such as a covalent bond, a hydrophobic bond or any other bond of equal strength. The antibody is one against the Fc region of an immunoglobulin. There may be used either polyclonal or monoclonal antibodies which have properties as set out in detail hereinafter.

The A-B-C- conjugate binds selectively the entity, such as enzyme, towards which the C antibody is specific. The finally obtained conjugate can be used for quantitation of enzymes or for effecting enzymatic processes.

The A-B- conjugate is a basic entity, and to it there can be bonded a wide variety of antibodies, specific towards the entity which is to be determined, or the activity of which is to be used.

The carrier bound antibody can be used for selectively extracting a specific enzyme from body fluids, and to bind them in a manner where the full enzymatic activity is retained. The combination of A-B-defined above is adapted to bind any desired type of antibody, be it from mice, rabbit, human or other source. There can be provided as commercial product the A-B conjugate, together with one or more antibodies, which can be bound to the A-B moiety according the the specific needs. This provides a great flexibility, and thus there can be provided means for selectively binding a variety of specific enzymes, according to the C moiety chosen in the A-B-C entity. The high specificity of the C antibody results in a very high degree of specificity of the carrier bound antibody. The insertion of the B moiety considerably enhances the specificity and specific activity of the final product; it also provides for universality, versatility and flexibility.

The solid carrier A can be chosen from a wide variety of suitable solids, such as SEPHAROSE, a trademark owned by Pharmacia, Inc., Piscataway, N.J., for gel filtration media, EUPERGIT C, a trademark owned by Rohm Pharma, Weiterstadt, Germany, for oxirane acrylic beads, Polystyrene, polyamides, polyacrylamide gels, glass, polyvinylpyrrolidone etc. The various polymers can be provided as solid members, plates, tubes, hollow fibers, fibers, beads etc. Part B is a specific antibody, which is specific for the Fc region of a chosen immunoglobulin. This may be mouse, rabbit or human immunoglobulin; such immunoglobulin can be if necessary, species specific. The bonding of B to A can be a stable chemical bond (covalent bond) or there can also be used hydrophobic dissolution of two hydrophobic moieties. Binding ought to be of adequate strength, and amongst various possibilities there may be mentioned, as the B constituent:

1. Polyclonal antibodies:

Anti-mouse antibodies can be prepared by injection into any suitable animal; the polyclonal antibody can be prepared against the Fc region (mouse), in a similar manner it can be prepared against the human Fc region.

2. Monoclonal antibodies:

There can be prepared monoclonal antibodies adapted to recognize the Fc region of a desired mammal (mouse, rabbit, human) immunoglobulin and not to react with any other interfering species of immunoglobulins.

THE C ENTITY: ANTIBODY FOR ENZYME BINDING

There is provided an antibody preparation adapted to bind to a specific enzyme in such manner as not to adversely affect its enzymatic activity.

The binding ought to be of adequate strength and this can be attained by a suitable choice. The affinity to the enzyme ought to be high (of the order of $>10^8 M^{-1}$) and thus the binding to the enzyme or isoenzyme will be of adequate strength.

This applies both to monoclonal as well as to polyclonal antibodies.

Experiments have shown that such high strength binding can be obtained without essentially any loss of activity.

As set out above, entity C of the A-B-C- conjugate may be a tailor-made antibody specific towards any requires entity which elicits antibody formation by conventional procedures. Thus, the C-entity can be specific towards certain entities which are to be removed from body liquids, such as serum or the like. It is advantageous to use for this purpose monoclonal antibodies of high specificity towards the entity to be removed. Such system can be used, for example, for the removal of drugs of certain types and of other suitable materials from human serum, which can be subsequently returned to the body of the patient.

The entity A-B-C-E- defined above is characterized by a high degree of stability and enzymatic activity. The activity of the enzyme bound can be used for a quantitative assay of same enzyme. The preparation can also be used in columns or in other forms for effecting enzymatic conversions, as is conventional with carrier-bound enzymes. The following examples illustrate the present invention. These are to be constructed in an illustrative, non-restrictive manner.

EXAMPLE 1

Immobilized Carboxypeptidase (CPA)

The desired mAb to CPA was prepared and purified according to standard procedures. It was bound covalently to EUPERGIT C oxirane acrylic beads via the oxirane active groups of the polymer (see FIG. 1), or to SEPHAROSE gel filtration media-Protein A via the Fc fragment of the antibody. Carboxypeptidase A was then reacted with the conjugates of EUPERGIT C oxirane acrylic beads-mAb or SEPHAROSE gel filtration media Protein A-mAb to yield immobilized carboxypeptidase A preparations in which practically all of the bound enzyme molecules retained their full catalytic activity. The resulting preparation of EUPERGIT C oxirane acrylic beads-mAb-CPA and SEPHAROSE gel filtration media-Protein A-mAb-CPA retained practically all of their original activity following prolonged storage in the cold.

Immobilization of porcine lactate dehydrogenase (isoenzyme-5; LDH-5) was carried out as follows: Mouse hybridoma cells excreting monoclonal antibodies to the enzyme were prepared in the usual way. Those producing monoclonal antibodies which bind to the enzyme with high affinity without affecting its activity were isolated. At the same time a goat-antimouse IgG (Fc)-Eupergit C conjugate (Eupergit C-GAMIgG(Fc) was prepared. The latter was reacted with the desired mouse mAb present in the supernatant in which the selected and isolated hybridoma had been cultivated, to yield Eupergit C-GAMIgG (Fc)-mAb conjugate. The conjugate was found to react readily with the LDH-5 isoenzyme to yield the complex Eupergit C-GAMIgG(Fc)-mAb-LDH-5. All of the immobilized LDH-5-molecules were found to retain their original activity, most of which was maintained for several months when kept in the cold.

Carboxypeptidase A (CPA) was obtained as an aqueous crystal suspension (Sigma Chemical Co., St. Louis, Mo., USA). The crystals were washed with double-distilled water, centrifuged and dissolved in 0.05 M Tris-HCl/0.5 M NaCl buffer, pH 7.5. Insoluble material was removed by centrifugation. The protein concentration was derived from the absorbance at 278 nm, using a Perkin-Elmer spectrophotometer Model 550-S. Molar absorptivity for native CPA at 278 nm was assumed to be $6.42 \times 10^4 M^{-1} cm^{-1}$. The protein concentration was also determined by the Bradford method[1], using bovine serum albumin (BSA) as a standard.

EUPERGIT C oxirane acrylic beads were obtained from Rohm-Pharma GmbH, Darmstadt, FRG, and stored at −18° as recommended by the manufacturer. The beads were found to contain 800–1000 micromole of oxirane groups per 1 g dry weight, as determined by Axen's thiosulfate method[2]. They were found to contain some adsorbed acetone. Since the latter displays considerable absorption at 278 nm, it is recommended to wash the beads with distilled water until the washings show no detectable absorption at 278 nm.

Protein A-SEPHAROSE gel filtration media CL-4B was obtained from Pharmacia Fine Chemicals, Uppsala, Sweden. One gram of dry material swells in 0.1 M phosphate buffer, pH 8.0 to yield 3.5 ml of gel containing 2 mg of Protein A per ml.

ASSAY OF THE ENZYMIC ACTIVITY OF NATIVE AND IMMOBILIZED CARBOXYPEPTIDASE A

The enzymic activities of CPA and its derivatives were determined spectrophotometrically at 254 nm and 25° C. according to Whitaker et al,[3] using $10^{-3}$ M hippuryl-L-phenylalanine in 0.05 M Tris-HCl/0.5 M NaCl buffer pH 7.5 as peptidase substrate, and $10^{-3}$ M hippuryl-DL-$\beta$-phenyl lactic acid in the same buffer as esterase substrate. The recommended assay mixture contains 2 $\mu$g CPA per 1 ml of substrate solution. One unit of peptidase or esterase activity was defined as the amount of enzyme which catalyzes the hydrolysis of 1 micromole of substrate per min under the specified conditions. The specific activity of the native CPA used was 270 esterase units/mg and 56 peptidase units/mg. The catalytic activity of the immobilized CPA was determined by adding an amount of immobilized enzyme containing 2 $\mu$g of bound enzyme to 1 ml of standard substrate solution ($10^{-3}$ M hippuryl-L-phenylalanine or hippuryl-DL-$\beta$-phenyl lactic acid in 0.05 M Tris-HCl/0.5 M NaCl buffer, pH 7.5), shaking for 1 min at room temperature, centrifuging off the immobilized enzyme, and reading the increase in absorbance at 254 nm.

PREPARATION OF A MONOCLONAL ANTIBODY TO CARBOXYPEPTIDASE WHICH DOES NOT AFFECT ITS ENZYMIC ACTIVITY

Mouse monoclonal antibodies to CPA were prepared according to the procedure described, following the well-known fusion technique of Köhler and Milstein[4]. The supernatants of the growing hybridoma cells were collected and tested for binding to CPA using an ELISA procedure. Hybridomas producing supernatants with relatively high titers were selected, cloned and used for the preparation of the corresponding ascitic fluids. The monoclonal antibodies present in these ascitic fluids were then isolated by precipitation with 50% ammonium sulfate and their binding constants with CPA determined by means of a modified ELISA technique using beta-galactosidase conjugated with F(ab)$_2$ fragments of sheep antimouse IgG as a second antibody. The monoclonal antibody (mAb) chosen for enzyme immobilization displayed a binding constant of $\sim 10^9 M^{-1}$ and did not affect either the peptidase or the esterase activities of CPA. Its chemical nature was identified as IgG$_1$ by the Ouchterlony double immunodiffusion test. It could thus be purified chromatographically using a Protein A-SEPHAROSE gel filtration media affinity column.[5]. Elution of the IgG$_1$ subclass was carried out at pH 6.0 using 0.1 M citrate buffer. The resulting peak monitored by measuring protein absorption at 280 nm was collected, brought to pH 8.0, concentrated by ultrafiltration using a Diaflo PM30 membrane, and rechromatographed as above. Ten ml of the selected ascitic fluid yielded 10 mg of purified monoclonal antibody (mAb).

The effect of the purified mAb on the enzymic activity of CPA was determined as follows: The enzyme (2 $\mu$g in 2 $\mu$l of 0.05 M Tris-HCl/0.5 M NaCl buffer, pH 7.5) was incubated for 1 hr at room temperature with increasing amounts of the purified mAb (10–100 $\mu$g in 100 $\mu$l of the same buffer). The peptidase and esterase activities of the incubation mixture were assayed as described above. No effect on either of the enzymic activities could be detected even at the highest mAb concentrations employed.

It should be noted in this connection that all of the tested ascitic fluids containing the various monoclonal antibody preparations, inhibited nonspecifically both the peptidase and the esterase activities of CPA. Purification of the monoclonal antibodies was thus required in this case in order to determine the nature of the interaction between CPA and its monoclonal antibodies.

PREPARATION OF EUPERGIT C-MONOCLONAL ANTIBODY-CARBOXYPEPTIDASE A COMPLEX (EUPERGIT C OXIRANE ACRYLIC BEADS-mAb-CPA)

EUPERGIT C oxirane acrylic beads (100 mg) was added to a solution of purified mAb (1 mg) in 0.1 M phosphate buffer, pH 8.0 (1 ml), and the resulting suspension was left for 24 hr at room temperature. Practically all of the antibody was bound to the carrier towards the end of this period. The EUPERGIT C oxirane acrylic beads-mAb complex was separated by centrifugation, and the remaining oxirane active groups were blocked by incubation with 10% ethanolamine, pH 9.0 (1 ml) for a further 24 hr at room temperature. The immobilized antibody preparation obtained was washed repeatedly with distilled water and finally equilibrated with phosphate buffered saline (PBS). The final suspension of EUPERGIT C oxirane acrylic beads-mAb in PBS (0.8 ml) was incubated with CPA (400 $\mu$g) in 0.5 M NaCl (0.2 ml) for 1 hr at room temperature. The amount of protein immobilized on the carrier was calculated from the difference between the initial amount of protein in the reaction mixture, as determined by the Bradford test, and that found in the supernatant after coupling. Approximately 50% of the initial amount of enzyme was immobilized under the experimental conditions specified. Similar results were derived from the difference between the initial enzyme activity and that left in the supernatant after coupling. Assay of the peptidase and esterase activities of the immobilized CPA revealed that the bound enzyme retains practically all of its original catalytic activity. The immobilized CPA preparation thus obtained, when stored in PBS at 4° C., was found to retain almost all of its initial activity for several months.

PREPARATION OF SEPHAROSE GEL FILTRATION MEDIA-PROTEIN A-MONOCLONAL ANTIBODY-CARBOXYPEPTIDASE A COMPLEX (SEPHAROSE GEL FILTRATION MEDIA-PROTEIN A-mAb-CPA)

SEPHAROSE gel filtration media-Protein A beads (100 mg in 1 ml of 0.1 M phosphate buffer, pH 8.0) were mixed with ascitic fluid (400 $\mu$l containing 400 $\mu$g of the mAb) and the mixture was incubated for 1 hr at room temperature. The beads containing the bound antibody were centrifuged and washed with the above phosphate buffer until the washings showed no detectable absorption at 280 nm. CPA (100 $\mu$g) in 0.1 M phosphate buffer, pH 8.0, (150 $\mu$l) was added to the SEPHAROSE gel filtration media-Protein A-mAb beads suspended in the same buffer (1 ml), and the reaction mixture shaken for an hour at room temperature. The amount of unreacted enzyme was determined by assaying the enzymic activity or protein left in the supernatant after centrifugation. Approximately 20% of the original enzymic activity (or of initial protein content) was found in the supernatant under the experimental conditions employed. Assay of the enzymic activity of the SEPHAROSE gel filtration media-Protein A-mAb-CPA beads revealed that practically all of the bound enzyme retains its original peptidase and esterase activities. The immobilized CPA preparation thus obtained was found to retain most of its initial enzymic activity for several months when stored in 0.1 M phosphate buffer, pH 8.0, at 4° C.

SOME CHARACTERISTIC PROPERTIES OF THE IMMOBILIZED CARBOXYPEPTIDASE A-MONOCLONAL ANTIBODY PREPARATIONS

Analysis of the kinetics of hydrolysis of hippuryl-L-phenylalanine and hippuryl-DL-β-phenyl lactic acid by EUPERGIT C oxirane acrylic beads-mAb-CPA or by SEPHAROSE gel filtration media-Proten A-mAb-CPA revealed that the characteristic kinetic parameters $K_M$ and $V_{max}$ for both immobilized CPA preparations are the same and closely resemble the corresponding parameters recorded in the literature for the native enzyme ($K_M = (2.6-4.0) \times 10^{-4}$ M and $V_{max} = (5.0-9.0) \times 10^{-5}$ M/min per mg enzyme for the peptidase activity and $K_M = (7.9-9.0) \times 10^{-5}$ M and $V_{max} = (2.0-5.0) \times 10^{-4}$ M/min per mg enzyme for the esterase activity). The effect of phenylpropionic acid on the activities of both immobilized CPA preparations was similar to its effect on the native enzyme, i.e., it behaved as a competitive inhibitor with respect to the peptidase activity and as a noncompetitive inhibitor with respect to the esterase activity. Following incubation for 2 hr at 50° C. the EUPERGIT C oxirane acrylic beads-mAb-CPA suspended in PBS lost 40% of its original activity, the SEPHAROSE gel filtration media-Protein A-mAb-CPA suspended in 0.1 M phosphate buffer, pH 8.0, lost 65% of its original activity, while the native CPA in solution (PBS, pH 7.4) lost approxmately 80% of its original activity. The pH activity curve of EUPERGIT C oxirane acrylic beads-mAb-CPA was found to be rather similar to that of the native enzyme, but its stability in the pH range 4.5-7.5 was somewhat greater. The pH activity and stability of SEPHAROSE gel filtration media-Protein A-mAb-CPA cannot be measured below pH 6.0 because of the dissociation of the mAb-Protein A complex.

IMMOBILIZATION OF LACTIC ACID DEHYDROGENASE

Materials

Porcine Lactate Dehydrogenase (Isoenzyme-5; LDH-5) Type XXXII (E.C. 1.1.1.27), Sodium Pyruvate and NDH were purchased from Sigma Chemical Co., St. Louis, Mo., USA. The enzyme was obtained as a crystalline suspension in ammonium sulfate. Since high dilutions of enzyme in PBS, pH 7.5, were employed no dialysis of the ammonium sulfate was found necessary.

Different tetrameric LDH isoenzymes are known.[6] The following isoenzymes consisting of the subunit M (muscle) and H (heart) have been characterized: LDH-1 = $H_4$; LDH-2 = $H_3M$; LDH-3 = $H_2M_2$; LDH-4 = $HM_3$ and LDH-5 = $M_4$. LDH-5 was used in the immobilization procedure described below.

The enzymic activity of native LDH was assayed according to Kornberg,[7] following the decrease in absorbance at 340 nm, as a result of the oxidation of NADH in the presence of pyruvate.

The activity of the immobilized enzyme was determined as follows: 100 μl of immobilized enzyme suspension containing approximately 1.5 μg of bound LDH-protein was added to 1 ml of the pyruvate/NADH assay solution.[7] The mixture was vortexed for 1-2 sec at room temperature and then left for 40 sec at 37°. The immobilized enzyme was centrifuged off at 10,000 g within one minute at room temperature, and its enzymic activity calculated from the decrease in absorbance at 340 nm.

Goat Antimouse IgG (Fc) Serum was purchased from Bio-Yeda, Kiryat Weizmann, Rehovot, Israel. According to the manufacturer it contains 4.7 mg of antimouse IgG per ml serum. Purified goat IgG (GA-MIgG) (~95%) was obtained by treatment of the serum with DEAE-cellulose (DE-52, purchased from Whatman Biochemicals, Springfield Mill, Maidstone, Kent, England), according to Stanworth.[8]

EUPERGIT C oxirane acrylic beads. The characteristic properties of this insoluble polymer carrier are described in the previous section dealing with the preparation of immobilized CPA. In the various EUPERGIT C oxirane acrylic beads preparations described in this section, removal of adsorbed acetone was not carried out. Protein content was determined in all cases by the Bradford assay,[1] since the marked adsorption of acetone at 280 nm prevented the derivation of protein content from absorbance at this wavelength. Separation of EUPERGIT C oxirane acrylic beads, as well as of its various derivatives to be described, from the liquid phase in which they had been suspended, was carried out (unless otherwise stated) by centrifugation at 1,500 g for 10 min at room temperature.

Preparation of Hybridoma Culture Media Containing Monoclonal Antibodies to LDH-5

Mouse monoclonal antibodies to LDH-5 were prepared according to the procedure of Köhler and Milstein,[9] utilizing the immunization procedure recommended by Stahli et al.[10] The hybridoma cells secreting the monoclonal antibodies to LDH-5 were grown in a Dulbecco modified Eagle's medium, supplemented with 10% horse serum. The presence of the monoclonal antibodies was tested for by the ELISA method, and only monoclonal antibodies (mAbs) containing supernatants which did not affect enzyme activity were chosen for further investigation.

Binding constants for the binding of LDH-5 to the monoclonal antibody preparations were determined according to Scatchard.[11] Separation between bound and free antigen (LDH-5) was performed by the double antibody solid phase (DASP) method,[12] using GA-MIgG attached to EUPERGIT C oxirane acrylic beads as the solid phase reagent (see below). The concentrations of monoclonal antibody in the various hybridoma culture media obtained were determined nephelometrically.[13] Independent evaluation of the concentrations of monoclonal antibody could also be obtained from the data acquired in the Scatchard plot experiments described above. The immunoglobulin type of the monoclonal antibodies obtained was determined by the standard Ouchterlony double immunodiffusion method.[14]

Two hybridoma supernatants were chosen as a source for the monoclonal antibodies used in the preparation of the immobilized LDH-5 samples to be described. Supernatant I was found to contain 45 μg of mAb of the type IgG1 per ml supernatant, with a binding constant of $5 \times 10^8 M^{-1}$ with LDH-5. Supernatant II was found to contain 20 μg of mAb of the type IgG2A per ml supernatant, with a binding constant of $1 \times 10^9 M^{-1}$ with LDH-5.

EUPERGIT C oxirane acrylic beads-Goat Antimouse (IgG(Fc) (EUPERGIT C oxirane acrylic beads-GAMIgG)

The purified GAMIgG fraction was dissolved in PBS, pH 7.5, and the solution brought to a final optical density of 3.8 at 280 nm (corresponding to a protein concentration of 2.8 mg per ml). Four ml of this solution were then added to 1 g of dry EUPERGIT C oxirane acrylic beads. The thick suspension obtained was left for 48 hr at room temperature and then mixed with 4 ml of PBS, pH 7.5. The resulting EUPERGIT C oxirane acrylic beads-GAMIgG complex was centrifuged and the supernatant tested for remaining protein. Practically all of the protein was bound to the carrier under the experimental conditions employed. The EUPERGIT C oxirane acrylic beads-GAMIgG complex was washed extensively with PBS, pH 7.5, until the washings showed a negligible absorbance at 280 nm. Any excess of unreacted oxirane groups in the EUPERGIT C oxirane acrylic beads-GAMIgG pellet was neutralized by the addition of 10 ml of 10% aqueous ethanolamine brought to approximately pH 9.0 with concentrated HCl. The final mixture was adjusted to pH 9.0 and the resulting suspension stirred gently overnight at 4° C. The final conjugate was centrifuged and washed repeatedly with PBS, pH 7.5, until the pH of the washings was the same as that of the buffer.

A crude preparation of EUPERGIT C oxirane acrylic beads-GAMIgG(Fc) could be obtained by reacting the polymer-carrier directly with an adequate volume of the goat antimouse serum under the conditions described above. It should be noted, however, that the crude carrier conjugate displayed considerably lower potency (per 1 g) for binding of murine monoclonal antibodies than that recorded for the product of coupling of Eupergit C with purified goat antimouse IgG. The EUPERGIT C oxirane acrylic beads-GAMIgG preparations were kept in suspension in PBS, pH 7.5, in the cold. Their binding capacity for murine antibodies remained unchanged even after storage for several months.

Immobilized LDH-5 of the Structure EUPERGIT C oxirane acrylic beads-Goat Antimouse IgG-Monoclonal Antibody-LDH-5 (EUPERGIT C oxirane acrylic beads-GAMIgG-mAb-LDH-5)

The EUPERGIT C oxirane acrylic beads-GAMIgG suspension in PBS, pH 7.5 (200 μl containing 25% per volume of active gel) was centrifuged and the pellet mixed with 0.4 ml of supernatant I or II (see section on the preparation of hybridoma culture media containing monoclonal antibody to LDH-5). The suspension obtained was incubated for 1 hr at 37° C. with shaking. The resulting EUPERGIT C oxirane acrylic beads-GAMIgG-mAb was centrifuged and washed with PBS, pH 7.5. Washings were repeated three times, using 6-ml portions of buffer for each washing. To the pellet was added 0.2 ml of a solution in PBS, pH 7.5, containing 180 μg LDH-5 and 1 mg BSA per 1 ml, and the suspension was incubated for 1 hr at 37° C. with shaking. The final conjugate obtained, consisting of EUPERGIT C oxirane acrylic beads-GAMIgG-mAb-LDH-5, was then centrifuged and washed with PBS, pH 7.5, as above. The pellet obtained after centrifugation was suspended in PBS, pH 7.5, and stored in the cold.

The amount of LDH-5 adsorbed by EUPERGIT C oxirane acrylic beads-GAMIgG-mAb to yield the final immobilized enzyme was calculated from the difference between the total enzymic activity in the initial reaction mixture and that left after adsorption. Practically all of the enzyme employed initially using Supernatant I or Supernatant II was adsorbed by the immobilized EUPERGIT C oxirane acrylic beads-mAb complex.

Assay of the enzyme activity of the EUPERGIT C oxirane acrylic beads-GAMIgG-mAb-LDH-5 preparations revealed that practically all of the bound enzyme retains full activity. Storage of the immobilized enzyme in PBS, pH 7.5, in the cold led to a decrease of 30% in activity within six months.

EXAMPLE

Carrier Bound Porcine Lactate Dehydrogen Isoenzyme 5 (PLDH5)

A glass column of 0.6 cm radius 2.7 cm height, was packed with 3 ml EUPERGIT C oxirane acrylic beads attached to Goat Polyclonal anti-Mouse IgG (1 Mg per 1 ml beads). A volume of 0.5 ml ascitic fluid containing monoclonal antibody against PLDH5 (2 mg) that does not affect the enzyme activity (binding constant of about $0.5 \times 10^8 M^{-1}$), was passed slowly (15 minutes) through the column at room temperature. The column was then washed with PBS pH 7.5 containing 0.1% Tween 20 until no significant absorbance of the eluate et 280 mm, could be detected. A volume of 2 ml PBS pH 7.5 containing PLDH5 (2 mg/ml) and bovine serum albumin (2 mg/ml) was the passed during 30 minutes through the column at room temperature. The column was washed with the same solution as above until practically no enzymatic activity could be detected in the eluate. Samples were then drawn from the column and the activity of the immobilized enzyme was checked. Full activity of the bound amount (total of 2 mg PLDH5 per 3 ml carrier) was retained on the carrier. The column was then washed with 30 ml of 0.2 M glycine - HCl pH 2.2 buffer and equilibrated with PBS until the PH of the eluate was the same as the pH of the applied buffer. The enzymatic activity of PLDH5 that remained attached to the carrier was checked on samples drawn from the column. No detectable activity was found at this stage.

Elution of Monoclonal Antibodies

The monoclonal antibodies against the enzyme were subsequently eluted This makes it possible to attach a different enzyme-specific antibody. The immobilization procedure from the monoclonal antibody immobilization step was repeated with a different antibody and continued as described above. The enzymatic activity of the enzyme thus immobilized after the second immobilization procedure, was checked. Full enzymatic activity of the immobilized enzyme was retained.

The product packed in a column may, when containing the right monoclonal antibody, serve as a means to extract and remove unwanted materials from solutions and render them suitable for chosen purposes.

As an example: it is possible to pass patient's serum through such column removing from it a poisonous drug or material and returning it afterwards into the patient's body.

The following experiment is a demonstration:

The use of the immunoadsorbent A-B-C- to extract enzyme from serum: In this experiment: A=EUPERGIT C oxirane acrylic beads, B=Species specific goat anti-mouse IgG (Pure antibodies), C=Purifies monoclonal antibodies against porcine LDH isoenzyme 5 (PLDH5) that do not affect enzymic activity and have binding constant of $5.6 \times 10^8 M^{-1}$, Enzyme=Porcine LDH isoenzyme 5 and the sera samples come from human or horse. Aliquats (0.1 ml) of various PLDH5 concentration (32-64 Mg/ml) were added to samples (1 ml) of human or horse serum. To each sample 125 Ml of immobilized monoclonal antibody ("A-B-C-") was added.

Suspensions were incubated at 37° C. with constant shaking, centrifuged and supernatant removed. Enzyme activities immobilized on the immunoadsorbent were measured. Almost all (99%) of the enzyme was removed from the sera that contained up to total concentration of 40 MG/ml in serum samples. Nearly 100% of the immobilized enzyme retained its activity on the A-B-C carrier.

REFERENCES

1. M. M. Bradford, Anal. Biochem. 72, 248 (1976)
2. L. Sundberg amd J. Porath, J. Chromat. 90, 87 (1974)
3. J. R. Whitaker, F. Menger and M. L. Bender, Biochemistry 5, 386 (1966)
4. B. Solomon, N. Moav, G. Pines and E. Katchalski-Katzir, Mol..Immunol. 21, 1 (1984).
5. P. L. Ey., S. J. Prowse and C. R. Jenkin, Immunochemistry 15, 429 (1978).
6. J. J. Holbroock, A. Liljas, S. J. Steindel, N. G. Rossmann, in "The Enzymes" (3rd ed.) (P. O. Boyer, ed.), Vol. XI, pp. 191-292, 1975.
7. A. Kornberg Meth in Enzym. 1, 441 (1955).
8. Stanworth, Nature 188, 156 (1960)
9. G. Köhler and C. Milstein, Nature 256, 495 (1975).
10. Stahli: J. Imm Methods 32 297 (1980)
11. Scatchard Ann. NY Acad Sci. 51 660 (1949)
12. B. K. Weenan et al. FEBS Letters 15 232 (1971)
13. J. Guldi et al. Int Arch Allergy & App Imm 60 186 (1979)
14. O. Ouchterlony and L. A. Nilsson, in "Handbook of Experimental Immunology" (D. M. Weir, ed.), Vol. 1, pp. 19.1-19.4, Blackwell, Canada, 1978.

We claim:

1. A composition which selectively binds a predetermined enzyme or isoenzyme which comprises the structure A-B.C wherein A is a water-insoluble carrier, B is a polyclonal anti-mouse antibody against the Fc region of monoclonal antibody C, C is a monoclonal mouse immunoglobulin antibody having an Fc region which binds only to a predetermined enzyme or isoenzyme by an immunochemical bond and becomes attached to the enzyme or isoenzyme at a specific site which does not impair the catalytic activity of the enzyme or isoenzyme, B being linked to A by a chemical covalent bond, and C being attached to B by an immunochemical bond.

2. The composition of claim 1 wherein the material of carrier A is selected from the group of materials consisting of water-insoluble polysaccharides, polyamides, polyvinylpyrrolidone, and glass.

3. The composition of claim 1 wherein the form of carrier A is selected from the group of forms consisting of plates, rods, tubes, particles, and fibers.

4. A method for the quantitative determination of a specific enzyme or isoenzyme which comprises reacting essentially the entire quantity of the specific enzyme or isoenzyme in an aqueous solution with an excess of a composition which comprises the structure A-B.C wherein A is a water-insoluble carrier, B is a polyclonal anti-mouse antibody against the Fc region of monoclonal antibody C, C is a monoclonal mouse immunoglobulin antibody having an Fc region which binds only to the specific enzyme or isoenzyme by an immunochemical bond and becomes attached to the specific enzyme or isoenzyme at a specific site which does not impair the catalytic activity of the specific enzyme or isoenzyme, B being linked to A by a chemical covalent bond, and C being attached to B by an immunochemical bond; and determining the quantity of the reacted enzyme or isoenzyme by determination of its catalytic activity.

5. The method of claim 4 wherein the enzyme is carboxypeptidase A.

6. The method of claim 4 wherein the isoenzyme is isoenzyme 5 of porcine lactate dehydrogenase (E.C. 1.1.1.27).

7. A method for the enzymatic conversion of a substrate comprising reacting an aqueous solution of the substrate with the entity resulting from the reaction of a specific enzyme and a composition which comprises the structure A-B.C wherein A is a water-insoluble carrier, B is a polyclonal anti-mouse antibody against the Fc region of monoclonal antibody of C, C is a monoclonal mouse immunoglobulin antibody having an Fc region which binds only to the specific enzyme by an immunochemical bond and becomes attached to the specific enzyme at a specific site which does not impair the catalytic activity of the specific enzyme, B being linked to A by a chemical covalent bond, and C being attached to B by an immunochemical bond.

8. The method of claim 7 wherein the entity is contained in a column.

* * * * *